US012788765B2

(12) United States Patent
Beniamino et al.

(10) Patent No.: US 12,788,765 B2
(45) Date of Patent: Nov. 10, 2026

(54) METHOD FOR ADMINISTRATION OF URSODEOXYCHOLIC ACID

(71) Applicant: SHILPA MEDICARE LIMITED, Raichur (IN)

(72) Inventors: Palmieri Beniamino, Modena (IT); Pradeep Shivakumar, Bengaluru (IN); Krishnamurthy Toppaladoddi, Bengaluru (IN)

(73) Assignee: SHILPA MEDICARE LIMITED, Raichur (IN)

(*) Notice: Subject to any disclaimer, the term of this patent is extended or adjusted under 35 U.S.C. 154(b) by 819 days.

(21) Appl. No.: 17/790,759

(22) PCT Filed: Jan. 21, 2021

(86) PCT No.: PCT/IB2021/050448
§ 371 (c)(1),
(2) Date: Jul. 5, 2022

(87) PCT Pub. No.: WO2021/152430
PCT Pub. Date: Aug. 5, 2021

(65) Prior Publication Data

US 2023/0016551 A1 Jan. 19, 2023

(30) Foreign Application Priority Data

Jan. 28, 2020 (IN) ............................ 202041003726

(51) Int. Cl.
*A61P 1/16* (2006.01)
*A61K 9/00* (2006.01)
*A61K 9/19* (2006.01)
*A61K 31/575* (2006.01)

(52) U.S. Cl.
CPC .......... *A61K 31/575* (2013.01); *A61K 9/0019* (2013.01); *A61P 1/16* (2018.01)

(58) Field of Classification Search
CPC ........ A61K 31/575; A61K 9/0019; A61P 1/16
See application file for complete search history.

(56) References Cited

U.S. PATENT DOCUMENTS

| | | | | | |
|---|---|---|---|---|---|
| 5,858,998 | A | 1/1999 | Leuschner | | |
| 5,955,456 | A * | 9/1999 | Prato | A61P 1/16 | 514/182 |
| 6,297,229 | B1 * | 10/2001 | Lindor | A61K 31/56 | 514/894 |
| 2009/0163459 | A1 * | 6/2009 | Trauner | A61P 37/00 | 514/182 |
| 2009/0170754 | A1 | 7/2009 | Larusso et al. | | |
| 2012/0071451 | A1 * | 3/2012 | Spenard | A61P 3/10 | 514/182 |
| 2021/0137858 | A1 * | 5/2021 | Cha | A61K 31/235 | |

FOREIGN PATENT DOCUMENTS

| | | | |
|---|---|---|---|
| CN | 101028274 | A | 9/2007 |
| KR | 20110131697 | A | 12/2011 |
| WO | WO-1994022896 | A1 | 10/1994 |
| WO | 2015142178 | A1 | 9/2015 |
| WO | WO-2021099973 | A1 | 5/2021 |

OTHER PUBLICATIONS

Silveira et al., "Primary sclerosing cholangitis," Can J Gastroenterol. Aug. 2008;22(8):689-98. (Year: 2008).*
Farrell et al., "NASH is an Inflammatory Disorder: Pathogenic, Prognostic and Therapeutic Implications," Gut Liver, Apr. 2012;6(2):149-71. (Year: 2012).*
Duerksen, D.R., et al., "Intravenous Ursodeoxycholic Acid Reduces Cholestasis in Parenterally Fed Newborn Piglets," Gastroenterology 111(4):1111-1117, W.B. Saunders, United States (Oct. 1996).
Galan, A.I., et al., "Effects of Ursodeoxycholate on Maximal Biliary Secretion of Bilirubin in the Rat," Biochemical Pharmacology 39(7):1175-1180, Elsevier Science, United Kingdom (Apr. 1990).
International Search Report and Written Opinion for International Application No. PCT/IB2021/050448, mailed on Mar. 31, 2021, 11 pages.

* cited by examiner

*Primary Examiner* — Jared Barsky
(74) *Attorney, Agent, or Firm* — Sterne, Kessler, Goldstein & Fox P.L.L.C.

(57) ABSTRACT

The present invention provides the method and/or compositions for administering a therapeutically effective amount of ursodeoxycholic acid (UDCA) intravenously for the treatment and/or the prevention of liver diseases, preferably chronic liver diseases. The present invention also relates to methods of intravenous administration of UDCA in a dose of about 15 mg/kg to about 200 mg/kg at a dosage interval of once every 12 hours to once every 72 hours.

7 Claims, 3 Drawing Sheets

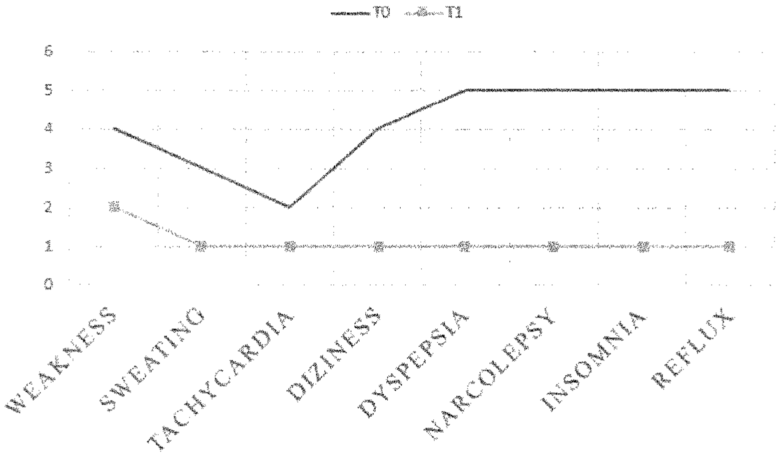
Figure 1: Symptoms at T0 (pre-treatment of UDCA) and T1 (after the intravenous administration of UDCA) in the intravenous group of 50 patients.
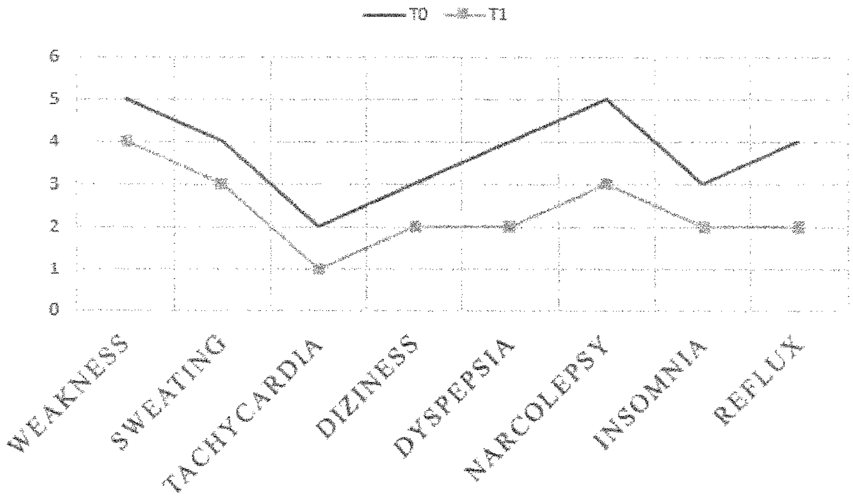
Figure 2: Symptoms at T0 (pre-treatment of UDCA) and T1 (after the oral administration of UDCA) in the intravenous group of 50 patients.

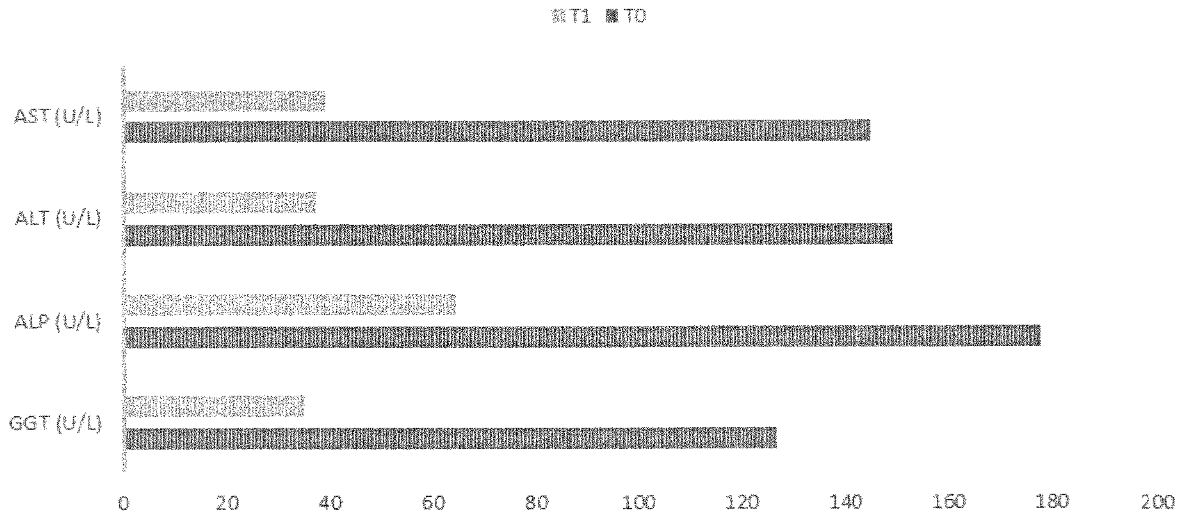
Figure 3: Liver Parameters at T0 (pre-treatment) and at T1 (after the treatment of intravenous UDCA) in patients with cancer chemotherapy and liver failure.
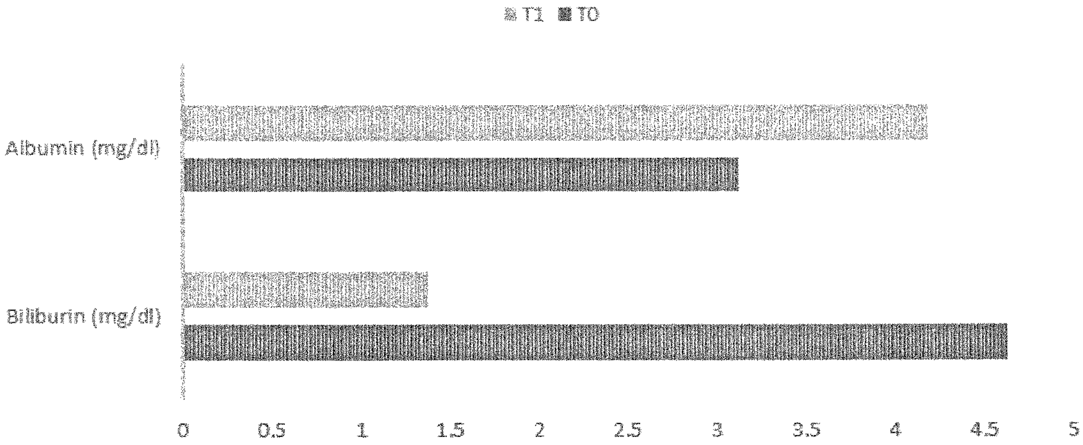
Figure 4: Bilirubin and Albumin at T0 (pre-treatment) and at T1 (after the treatment of intravenous UDCA) in patients with cancer chemotherapy and liver failure.

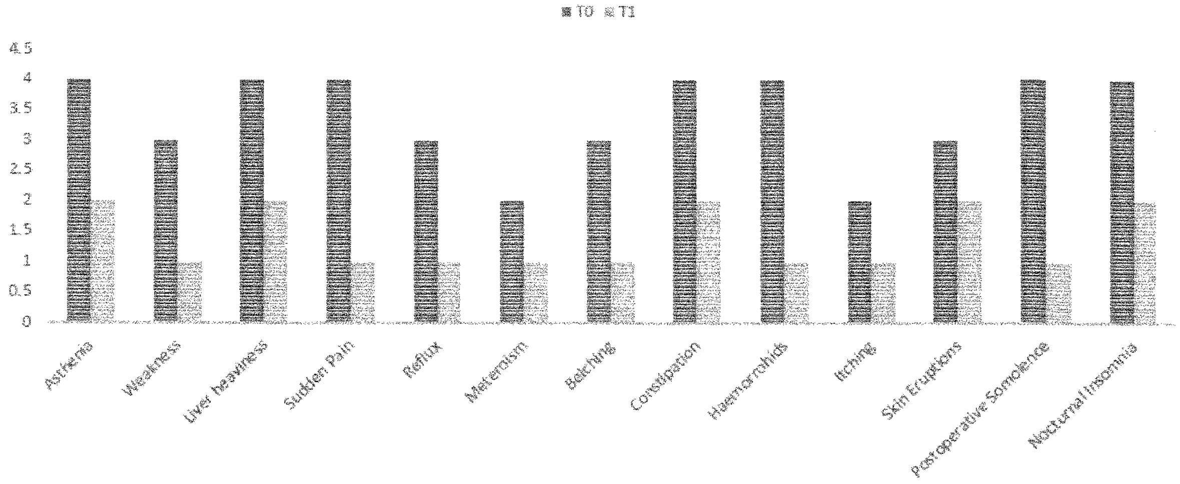
Figure 5: RSCL Symptoms comparision at T0 (pre-treatment) and T1 (after completion of treatment with intravenous UDCA at end of 3 weeks)

METHOD FOR ADMINISTRATION OF URSODEOXYCHOLIC ACID

FIELD OF THE INVENTION

The present invention relates to methods for administering a therapeutically effective amount of ursodeoxycholic acid (UDCA) intravenously for the treatment and/or the prevention of liver diseases, preferably chronic liver diseases. The present invention also relates to methods of intravenous administration of UDCA in a dose of about 15 mg/kg to about 200 mg/kg at a dosage interval of once every 12 hours to once every 72 hours.

BACKGROUND OF THE INVENTION

Ursodeoxycholic acid (UDCA), the naturally occurring bile acid, which can be found in small amounts in the bile and in blood of humans is widely used to treat liver diseases, wherein one of the most important indication areas of UDCA is the dissolution of gall stones and the treatment of primary biliary cirrhosis (PBC). UDCA is used in PBC at a dose of 13-15 mg/kg/day administered orally in two to four divided doses with food. UDCA is used in the dissolution of gall stones at a dose of 8-10 mg/kg/day administered orally in 2 or 3 divided doses.

The oral administration of UDCA has several gastrointestinal disorders like abdominal discomfort, abdominal pain, constipation, diarrhoea, dyspepsia, nausea and vomiting. The gastrointestinal disorders with UDCA administration orally is more critical in a greater number of patients with cancer undergoing chemotherapy.

In order to overcome the above disadvantages with the oral administration of UDCA, there exists a need for the pharmaceutical composition and/or methods for administering a therapeutically effective amount of UDCA and/or pharmaceutically acceptable salts or solvates or esters thereof intravenously for the treatment and/or the prevention of liver diseases, preferably chronic liver diseases.

SUMMARY OF THE INVENTION

The present invention provides the methods for administering a therapeutically effective amount of ursodeoxycholic acid (UDCA) and/or pharmaceutically acceptable salts or solvates or esters thereof, intravenously for the treatment and/or the prevention of liver diseases, preferably chronic liver diseases.

In the embodiments of the invention the liver diseases treated by intravenous administration of UDCA and/or pharmaceutically acceptable salts or solvates or esters thereof, are fatty and cholestatic liver diseases.

In embodiments of the invention fatty liver diseases treated with intravenous administration of UDCA and/or pharmaceutically acceptable salts or solvates or esters thereof, are non-alcoholic fatty liver disease (NAFLD) or non-alcoholic steatohepatitis (NASH) and alcoholic fatty liver disease (alcoholic steatohepatitis).

In a further embodiment of the invention cholestatic liver diseases treated with intravenous administration of UDCA and/or pharmaceutically acceptable salts or solvates or esters thereof, are primary sclerosing cholangitis (PSC), primary biliary cirrhosis (PBC), dissolution of gallstones, progressive familial intrahepatic cholestasis, or drug-induced cholestasis In an embodiment of the invention, the present invention provides the methods of intravenous administration of UDCA and/or pharmaceutically acceptable salts or solvates or esters thereof, in a dose of about 15 mg/kg to about 200 mg/kg at a dosage interval of once evert 12 hours to once every 72 hours.

BRIEF DESCRIPTION OF THE DRAWINGS

FIG. 1 discloses the symptoms of the patients treated for NAFLD with the intravenous administration of UDCA at T0 (pre-treatment) and T1 (after 24 intravenous infusions of UDCA at end of second month).

FIG. 2 discloses the symptoms of the patients treated for NAFLD with the oral administration of UDCA at T0 (pre-treatment) and T1 (after the oral administration UDCA at the end of 2 months).

FIG. 3 discloses the liver parameters at T0 (pre-treatment) and at T1 (after the intravenous treatment of UDCA at end of three weeks in ten sessions) in patients with cancer chemotherapy or liver failure.

FIG. 4 discloses the bilirubin and Albumin at T0 (pre-treatment) and at T1 (after the intravenous treatment of UDCA at end of three weeks in ten sessions) in patients with cancer chemotherapy or liver failure.

FIG. 5 discloses the RSCL Symptoms comparision at T0 (pre-treatment) and T1 (after completion of treatment with intravenous UDCA at end of three weeks in ten sessions) in patients with cancer chemotherapy or liver failure.

DETAILED DESCRIPTION OF THE INVENTION

The present invention provides the methods for administering a therapeutically effective amount of UDCA and/or pharmaceutically acceptable salts or solvates or esters thereof intravenously for the treatment and/or the prevention of liver diseases, preferably chronic liver diseases.

The liver disease to be treated with intravenous administration of UDCA and/or pharmaceutically acceptable salts or solvates or esters thereof according to the present invention is cholestatic liver disease, preferably primary biliary cholangitis (PSC), primary biliary cirrhosis (PSC) or dissolution of gallstones or progressive familial intrahepatic cholestasis type 1, 2 and 3, cystic fibrosis, drug induced cholestasis or a non-cholestatic liver disease such as chronic viral hepatitis (B, C, D), fatty liver diseases preferably non-alcoholic fatty liver disease (NAFLD) or non-alcoholic steatohepatitis (NASH) and alcoholic fatty liver disease (alcoholic steatohepatitis), hemochromatosis, Wilson disease and alpha-1-antitrypsin deficiency. Furthermore, intravenous administration of UDCA and/or pharmaceutically acceptable salts or solvates or esters thereof can be used for the prevention/chemoprevention of liver carcinoma, preferably hepatocellular carcinoma and cholangiocarcinoma. Even furthermore, intravenous administration of UDCA and/or pharmaceutically acceptable salts or solvates or esters thereof can be used for the chronic liver injury and also enzymatic dysfunction due to chemotherapy for cancer or liver multiple metastatic lesions with liver function impairment and parasitic infections (like schistosoma and leishmania).

In another embodiment, the liver diseases to be treated with intravenous administration of UDCA is acute liver insufficiency due to poisoning (chemical and dietary mushrooms). The acute liver insufficiency treatment with UDCA shall be used patients especially in critical conditions, where liver transplant is not available.

In a still further embodiment, UDCA is administered into the donor transplant liver cool perfusate during the transport of organ. Further UDCA is used to support the optimal liver donor/receipt functional integration, reduce the acute rejection flares, improve the general functions and bile flow.

According to the preferred embodiment of the present invention, the liver disease treated with intravenous administration of UDCA and/or pharmaceutically acceptable salts or solvates or esters thereof is primary biliary cholangitis (PSC), primary biliary cirrhosis (PBC), dissolution of gall bladder stones and bile duct stone. The dissolution of gall bladder stones and bile duct stones relives the colicky pain by dissolving the gall stones (cholesterol stones) and directly transfer them to the bile ducts stream.

In a further preferred embodiment of the present invention, the liver diseases treated with intravenous administration of UDCA and/or pharmaceutically acceptable salts or solvates or esters thereof is non-alcoholic fatty liver disease (NAFLD) or non-alcoholic steatohepatitis (NASH) and alcoholic fatty liver disease (alcoholic steatohepatitis).

In embodiments of the invention, the present invention provides the method for administration of UDCA comprising the step of administering intravenously to a human patient in need thereof a therapeutically effective amount of UDCA in a dose of about 15 mg/kg to about 200 mg/kg of UDCA, wherein the UDCA dose is repeatedly administered at a dosage interval of once every 12 hours to once every 72 hours.

In one embodiment of the instant invention, the dose is of about 15 mg/kg to about 200 mg/kg UDCA. In a preferred embodiment, the dose is of about 25 mg/kg to about 150 mg/kg. In a more preferred embodiment, the dose for human patients is of about 30 mg/kg to about 100 mg/kg. Doses that may include 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg. Other doses higher than, intermediate to or less than these doses shall be used for administering intravenously.

In further embodiments of the invention, the dose of about 15 mg/kg to about 200 mg/kg UDCA is used for the treatment of liver diseases, for the patients where the enterohepatic circulation is impaired, partially or totally interrupted or liver failure.

In a still further embodiments of the invention, UDCA is administered intravenously for the treatment of liver diseases with the patients having enterohepatic cycle dysfunction or block with intense replacement, gut partially or totally obstructing cancers, pancreatitis, ulcerative colitis and Chron's disease.

In one embodiment of the instant invention, the dosage interval is 12 hours to once weekly. In preferred embodiment, UDCA is administered at a dose interval of once every 12 hours, once every 24 hours, once every 48 hours, once every 60 hours, once every 68 hours, once every 72 hours, once every 84 hours and once every 96 hours or once weekly.

In embodiments of the invention UDCA may be administered according to the above until the liver diseases is eradicated or reduced. In one embodiment UDCA is administered for a period of time from about 3 days to about 12 months. In a preferred embodiment, UDCA is administered from about 5 days to about 6 months. UDCA may be administered for a longer or shorter period if so desired.

In another embodiment of the invention, the present invention provides a pharmaceutical composition comprising UDCA administered intravenously to a human patient in need thereof a therapeutically effective amount of UDCA in a dose of about 15 mg/kg to about 200 mg/kg of UDCA, wherein the UDCA dose is repeatedly administered at a dosage interval of once every 12 hours to once every 72 hours.

In another embodiment of the invention, the use of the invention is characterized by manufacture of a pharmaceutical composition comprising UDCA administered intravenously to a human patient in need thereof a therapeutically effective amount of UDCA in a dose of about 15 mg/kg to about 200 mg/kg of UDCA, wherein the UDCA dose is repeatedly administered at a dosage interval of once every 12 hours to once every 72 hours.

In another embodiment the present invention provides to use of UDCA for the manufacture of a medicament for treatment of human patient in need thereof, wherein a dose for said treatment is about 15 mg/kg to about 200 mg/kg of UDCA, wherein said dose is repeatedly administered at a dosage interval of once every 12 hours to once every 72 hours.

In a further embodiment the present invention provides a method for treating non-alcoholic steatohepatitis (NASH) in a human patient in need thereof, comprising the step of administering intravenously a therapeutically effective amount of UDCA in a dose of about 15 mg/kg to about 200 mg/kg of UDCA, wherein UDCA dose is repeatedly administered at a dosage interval of once every 12 hours to once every 48 hours.

In a still further embodiment the present invention provides a method for treatment and/or prevention of cholestatic liver disease in a human patient in need thereof, comprising the step of administering intravenously a therapeutically effective amount of UDCA in a dose of about 15 mg/kg to about 200 mg/kg of UDCA, wherein the UDCA is repeatedly administered at a dosage interval of once every 12 hours to once every 72 hours.

In further embodiments the present invention relates to a kit for treating a patient having cholestatic liver disease selected from the group consisting of primary sclerosing cholangitis (PSC), primary biliary cirrhosis (PBC) and dissolution of gall stones, comprising a therapeutically effective amount of composition comprising ursodeoxycholic acid (UDCA) in a dose of about 15 mg/kg to about 200 mg/kg of ursodeoxycholic acid (UDCA), intravenously. In a more preferred embodiment, the kit comprises a dose for human patients about 30 mg/kg to about 100 mg/kg. Doses includes 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg. Other doses higher than, intermediate to or less than these doses shall be used for administering intravenously. Further the dosage interval is at which the kit comprising UDCA is administered is 12 hours to once weekly. In preferred embodiment, UDCA is administered at a dose interval of once every 12 hours, once every 24 hours, once every 48 hours, once every 60 hours, once every 68 hours, once every 72 hours, once every 84 hours and once every 96 hours or once weekly.

In another embodiment the present invention relates to a kit for treating a patient having non-alcoholic steatohepatitis (NASH), comprising a therapeutically effective amount of composition comprising ursodeoxycholic acid (UDCA) in a dose of about 15 mg/kg to about 200 mg/kg of ursodeoxycholic acid (UDCA), intravenously. In a more preferred embodiment, the kit comprises a dose for human patients about 30 mg/kg to about 100 mg/kg. Doses includes 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg. Other doses higher than, intermediate to or less than these doses shall be used for administering intravenously. Further the dosage interval is at which the kit comprising UDCA is administered is 12 hours to once weekly. In preferred embodiment, UDCA is administered at a dose interval of once every 12 hours, once every 24 hours, once every 48 hours, once every 60 hours, once every 68 hours, once every 72 hours, once every 84 hours and once every 96 hours or once weekly.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1: Intravenous Administration of UDCA for the Treatment of Non-Alcoholic Fatty Liver (NAFLD) Disease Two groups of patients (each group consisting of 50 patients N=50 as disclosed in Table-1) with non-alcoholic fatty liver disease are taken and standardized with the diet of 1300 calories/day (30% proteins, 30% carbohydrates and 40% fat).

TABLE 1

| Baseline Characteristics | Intravenous UDCA (bile salt) administration group | Oral UDCA (bile salt) administration group |
|---|---|---|
| Age (years) | 40 ± 8.75 | 42 ± 9.42 |
| Females | 30 | 35 |
| Males | 20 | 15 |
| BMI (Body mass index kg/m$^2$) | 29.06 ± 4.6 | 28.18 ± 3.8 |
| Serum Total Cholesterol - Total CHL (mg/dl) | 145 ± 35.8 | 156 ± 22.6 |
| Serum Triglycerides (mg/dl) | 95 ± 35.2 | 110 ± 45.5 |
| Systolic blood pressure (mm hg) | 120 ± 8.2 | 115 ± 6.9 |
| Diastolic blood pressure (mm hg) | 84 ± 8.2 | 78 ± 9.0 |

The first group of patients was treated with 50 mg/kg/day UDCA orally for first two months (500 mg capsules swallowed after meals on average of 2-3 capsules after breakfast, 3-4 capsules after lunch and 3-4 capsules after dinner). The second group of patients was treated with intravenous schedule of UDCA at a dose of 3500 mg each other day (every 48 hours) for a total of 24 intravenous sessions. The lab examinations were performed at time T0 (beginning of the study) and time T1 (end of second month treatment). Each patient of the two groups was submitted to standard echo graphic classification as follows:

Grade 0: No fatty liver

Grade 1 (Mild): Mild diffuse increase in the echogenicity of liver parenchyma or increased hepatorenal contrast with normal diaphragm and intrahepatic vessel borders.

Grade 2 (Moderate): Moderate diffuse increase in the echogenicity of liver parenchyma and increased hepatorenal contrast with slight impairment of diaphragm and intrahepatic vessel borders.

Grade 3 (Severe): In addition to moderate steatosis there was no visualization of posterior portion of the right lobe of liver, intrahepatic vessel borders and diaphragm.

Values were presented as mean±standard deviation for quantitative variable and percentages for categorical variables. The two groups were compared by student's t-test for quantitative variable and chi-square for the categorical variables. Changes from baseline to 12 weeks were compared by paired t-test within each group. Wilcoxon test was used for rating variable comparison before and after treatment in each group.

To evaluate variation in symptoms pre (T0) and post-treatment (T1), a self-administered questionnaire was given to patients for answering consisting of type, frequency, intensity, and time of symptom. Scale ranging from 0 (minimal symptom) to 5 (severe symptom).

A. Histology Examination:

Only four patients in each group has accepted to undergo the liver biopsy (LB) before and after the treatment with intravenous UDCA and oral UDCA. In intravenous treatment group, regression of fat embedded liver a leucocytes infiltration into portal spaces cells was more evident than in the oral treatment group (results as disclosed in Table-2).

B. Elastography in Liver:

Ultrasound imaging plays a major role in the diagnosis, monitoring and therapeutic decisions of chronic liver diseases. It has many clinical indications: morphological examination of the liver parenchyma and assessment of the risk of chronic liver disease by investigating for signs of dysmorphism and/or portal hypertension; detecting and characterizing liver lesions; monitoring local treatments and assessment of treatment response. Different levels of fibrosis are assessed using a histological score. The most widely used is the METAVIR score, which incorporates five stages of fibrosis:

F0 (no fibrosis),

F1 (portal fibrosis without septa: minimal fibrosis),

F2 (portal fibrosis with a few septa: moderate fibrosis or clinically significant fibrosis), F3 (septal fibrosis with many septa but no cirrhosis: severe fibrosis) and F4 (cirrhosis).

Staging liver fibrosis in patients with chronic liver disease is essential for patient management as it allows:

1) To identify the severity of the liver damage in order to decide whether or not to start treatment (chronic viral liver disease) to avoid progression to cirrhosis when the fibrosis becomes significant (≥F2);
2) To assess the progression or regression of liver fibrosis during treatment;
3) To institute specific monitoring to screen for and treat complications (HCC, Esophageal varices) in patients suffering from cirrhosis and even severe fibrosis (≥F3).

Conventional ultrasound cannot differentiate accurately the different liver fibrosis stages. Existing tools to assess liver fibrosis include liver biopsy (LB), which is invasive, and other non-invasive methods. The main non-invasive method to assess liver fibrosis is based on a physical parameter that measures the tissue elasticity and is called Elastography. It can replace subjective palpation and is intended to image the mechanical properties of tissues and more particularly their stiffness. The Elastography methods are based on a common approach: measurement of deformation induced in a tissue by a force. This technique uses an external mechanical device or an internal acoustic radiation force (ARFI and SWE) to induce shear waves in the tissue to be explored. The diagnostic action mechanism is based on shear wave, which is generated by an external mechanical impulse and whose speed is measured by an ultrasound one-dimensional probe. The one-dimensional probe (3.5 MHz) is mounted along the axis of an electro-dynamic transducer (vibrator). In this way it is possible to define the liver stiffness by measuring the velocity of elastic shear waves in the liver parenchyma generated by the mechanical impulse. The propagation velocity is directly related to the stiffness of the medium, defined by the Young modulus. Stiff tissues exhibit higher shear wave velocities than soft tissues. The elasticity is expressed in kPa (kilopascals) and is measured at depth ranging from 25 to 65 mm in a 1×4 cm area: the assessed liver volume is therefore two hundred times greater than the volume examined in a liver biopsy (LB). The obtained values range from 2.5 kPa to 75 kPa. Mean liver elasticity in "normal" subject is 5.81±1.54 and 5.23±1.59 kPa respectively for men and women. The measurement is painless and does not take more than 5 to 10 minutes. The results of 4 patients who have accepted for biopsy are tabulated in Table-3 at T0 and T1.

E. Liver Parameters (GGT, AST and ALT) Comparision in Intravenous UDCA and Oral UDCA Group:

There is a significant reduction in liver parameters of GGT (Gamma-Glutamyl Transpeptidase), AST (Aspartate Aminotransferase) and ALT (Alanine Aminotransferase) in patients administered with intravenous UDCA as compared to oral UDCA. The results are tabulated in Table-4.

TABLE 4

| | Intravenous UDCA Theraphy group (n = 50) | | Oral UDCA Theraphy group (n = 50) | |
|---|---|---|---|---|
| Parameters | T0 | T1 | T0 | T1 |
| BMI (kg/m$^2$) | 29.06 ± 4.6 | 26.25 ± 6.2 | 28.18 ± 3.8 | 27.67 ± 4.2 |
| GGT | 19.52 ± 5.82 | 16.77 ± 7.76 | 22.7 ± 6.43 | 20.83 ± 7.56 |
| AST | 65.54 ± 4.56 | 44.56 ± 5.52 | 63.25 ± 5.43 | 59.43 ± 3.39 |
| ALT | 78.05 ± 5.52 | 52.6 ± 5.65 | 76.48 ± 4.95 | 74.32 ± 5.58 |
| Liver Ultrasound - G | 3 ± 2 | 1 ± 0 | 3 ± 2 | 2 ± 1 |

TABLE 2

| Histological results Kondell histology activity index (HAI) score | | | | | | | | | | | | | | | | |
|---|---|---|---|---|---|---|---|---|---|---|---|---|---|---|---|---|
| | Intravenous administration of UDCA | | | | | | | | Oral administration of UDCA | | | | | | | |
| | Periportal +/− bridging | | Intralobular | | Portal inflammation | | Fibrosis | | Periportal +/− bridging | | Intralobular | | Portal inflammation | | Fibrosis | |
| Patient | T0 | T1 | T0 | T1 | T0 | T1 | T0 | T1 | T0 | T1 | T0 | T1 | T0 | T1 | T0 | T1 |
| 1 | 3 | 1 | 0 | 0 | 3 | 1 | 3 | 2 | 1 | 1 | 0 | 0 | 3 | 2 | 4 | 3 |
| 2 | 2 | 0 | 0 | 0 | 2 | 0 | 3 | 1 | 3 | 1 | 0 | 0 | 2 | 1 | 4 | 2 |
| 3 | 1 | 0 | 0 | 0 | 2 | 0 | 4 | 1 | 2 | 1 | 0 | 0 | 2 | 2 | 4 | 3 |
| 4 | 1 | 0 | 0 | 0 | 3 | 2 | 4 | 1 | 1 | 1 | 0 | 0 | 3 | 2 | 3 | 2 |

C. Gastrointestinal Side Effects Comparision for Oral UDCA and Intravenous UDCA Treatment:

The oral burden of UDCA oral (oral bile salt theraphy) gave origin to diarrhoea in 38% of the patients, nausea 15%, bloating 20%, moderate colicky pain, reduced appetite (10%), whereas the intravenous administration of UDCA (intravenous bile salt theraphy) was tolerated and preferred in terms of compliance compared with the capsules to be swallowed. No local or systemic side effects were noted during and after the intravenous administration of UDCA.

D. Weakness, Sweating, Tachycardia, Dizziness, Dyspepsia, Narcolepsy, Insomina and Reflux Symptoms Comparision for Oral and Intravenous UDCA Treatment:

Based on the questionnaire for the intravenous UDCA treatment all the patients evidenced improvement of symptoms, such as narcolepsy, weakness, sweating, tachycardia, dizziness, dyspepsia, insomnia, reflux which was more quickly and efficiently controlled since the first month of therapy whereas in the orally UDCA treatment group the symptoms improvement started later and were less marked. The symptoms of intravenous UDCA and oral UDCA treatment are disclosed in FIG. 1 and FIG. 2 respectively.

TABLE 3

| Electrography, kPa (mean ± standard deviation) | | | | |
|---|---|---|---|---|
| METAVIR | Intravenous administration of UDCA (parenteral bile salt theraphy) | | Oral administration of UDCA (Oral bile salt therapy) | |
| score | T0 | T1 | T0 | T1 |
| F ≥ 3 | 20.2 ± 5.7 | 9.9 ± 5.6 | 19.9 ± 7.1 | 12.5 ± 6.9 |
| F ≥ 4 | 25.3 ± 6.5 | 18.5 ± 5.9 | 23.6 ± 6.8 | 19.7 ± 5.8 |

Example 2: Intravenous Administration of UDCA During Cancer Chemotherapy and Liver Failure in Patients with Liver Diseases 100 patients with coexisting synchronous metachronous liver metastasis and liver enzymes/bilirubin impairment undergoing cancer chemotherapy and liver failure are taken and standardized with 3500 mg of UDCA infused intravenously for a total of ten sessions in 3 weeks (once every 68 hours). Nausea and vomiting were recorded daily on a diary card while quality of life was assessed, before treatment and at the end, using the Rotterdam Symptom Checklist (RSCL) questionnaire. Asthenia, weakness, heaviness and pain in the right hypochondrium biliary colicks, post-prandial somnolence, nocturnal insomnia, reflux, meteorism and belching, constipation symptomatic hemorrhoids, itching, and skin eruptions, dermographism were evaluated and the scores given in the RSCL Symptom Checklist are 1 (not at all), 2 (a little), 3 (quite a bit), 4 (very much): the higher the score, the higher the symptoms intensity and poor life quality.

The results showed the overall fair response of the liver insufficiency symptoms with intravenous UDCA and the functional lab exam markedly improved, especially transaminase and bilirubin. GGT, ALP (Alkaline Phosphatase), ALT, ASP parameters measured before the administration of UDCA (T0) and after 3 weeks on administration of UDCA (T1) are represented in FIG. 3. Bilirubin was variably decreased and albumin synthesis was variably increased after the intravenous administration of UDCA (T1) as represented in FIG. 4. The positive response to intravenous UDCA delivery was observed either in the chemo-intoxicated patients, or in multi metastatic liver colonization and largely depended by the amount of not invaded liver parenchyma. The life quality evaluated by RSCL Symptoms comparison at T0 (pre-treatment) and T1 (after completion of treatment with intravenous UDCA at end of 3 weeks) is disclosed in FIG. 5. Overall the patients affected by cancer with gut function impairment, and liver dysfunction due either to chemotherapy toxicity, liver metastasis, or paraneoplastic effects have a very poor life quality that can effectively be improved by administration of UDCA in parenteral route (intravenous), because the oral delivery wouldn't reach adequate absorption rate and would potentially generate adverse effects.

Example 3: Intravenous Administration of UDCA for Dissolution of Gallbladder Transparent Stone and Colicky Pains 20 patients were recruited aged 35 years to 65 years with sudden burst of biliary colicky pain due to radiolucent gallstones, diameter 0.3 to 0.9 mm and altered liver enzymes. Some patients are also icteric complaining of quite an intense pain with nausea and vomiting but without fever, negative inflammation markers (ESR, CRP) and slight leukocytosis, no rebound tenderness at the gallbladder manual exploration.

First 20 patients were administered with 3500 mg of UDCA every 12 hours for 6 days from the cubital vein; the very first infusion at the admission was added with 20 mg hyoscine-N-butyl bromide and 75 mg diclofenac as the patients are distressed by excruciating pain. At the end of first week the colic pain had completely subsided, then the patients were subdivided into two groups each containing 10 patients (as depicted in Table-5), the first group was administered intravenously with 3500 mg (50 mg/kg body weight for an average 70 kg patient) of UDCA twice a week (once every 84 hours) for a period of 3 months (24 infusions in total) and the second group was administered with 0.7 g/kg oral UDCA for a period of three months.

TABLE 5

| Baseline Characteristics | Intravenous UDCA (bile salt) administration group (n= 10) | Oral UDCA (bile salt) administration group (n = 10) |
|---|---|---|
| Age (years) | 30-55 years | 35-65 years |
| Females | 6 | 4 |
| Males | 4 | 6 |
| BMI (Body mass index kg/m$^2$) | 29.06 ± 4.6 | 28.18 ± 3.8 |

In the first week treatment with the intravenous administration of UDCA for 20 patients in a symptomatic theraphy with one ampoule of antispasmodic hyoscine-N-butyl bromide (20 mg) and diclofenac (75 mg) was added the colicky pain never relapsed along the week and the patients felt better since the second day of the therapy when they re-started oral feeding and no adverse effects of parenteral treatment were recorded.

After the first week, when the patients were divided into two groups for the oral and intravenous UDCA theraphy, in the oral group the colicky pain reappeared in 4 patients out of 10, during the first 40 days but not in the intravenous administration group. By the echo graphic evaluation of the gall stones, the gall stones dissolution was present in 7 patients of the intravenous group and in 3 patients of the oral group. In the parenteral group the remaining 3 patients showed reduction of the sludging concretions and overall stones volume more than 50% compared with the pre-treatment imaging. The oral UDCA group the remaining patients showed less than 30% average stones volume reduction.

We claim:

1. A method for treating non-alcoholic steatohepatitis (NASH) in a human patient in need thereof, consisting of administering intravenously a ursodeoxycholic acid (UDCA) as the only active agent in a dose of about 50 mg/kg to about 200 mg/kg of ursodeoxycholic acid (UDCA), wherein the ursodeoxycholic acid (UDCA) dose is repeatedly administered at a dosage interval of once every 12 hours to once every 48 hours, and wherein the UDCA is not formulated for sustained release.

2. The method according to claim 1, wherein ursodeoxycholic acid (UDCA) is administered for about 5 days to about 6 months.

3. A method for treating cholestatic liver disease in a human patient in need thereof, consisting of administering intravenously a ursodeoxycholic acid (UDCA) as the only active agent in a dose of about 50 mg/kg to about 200 mg/kg of ursodeoxycholic acid (UDCA), wherein the ursodeoxycholic acid dose (UDCA) is repeatedly administered at a dosage interval of once every 12 hours to once every 84 hours, and wherein the UDCA is not formulated for sustained release.

4. The method according to claim 3, wherein the cholestatic liver disease is selected from group consisting of primary sclerosing cholangitis (PSC), primary biliary cirrhosis (PBC) and gall stones.

5. The method according to claim 3, wherein ursodeoxycholic acid (UDCA) is administered for about 5 days to about 6 months.

6. The method of claim 1, wherein the UDCA is administered in an amount of about 3500 mg.

7. The method of claim 3, wherein the UDCA is administered in an amount of about 3500 mg.

* * * * *